(12) United States Patent
Yoshimura et al.

(10) Patent No.: US 9,815,973 B2
(45) Date of Patent: Nov. 14, 2017

(54) EPOXY ESTER COMPOUND, CELLULOSE ESTER RESIN COMPOSITION, OPTICAL FILM, AND LIQUID-CRYSTAL DISPLAY DEVICE

(71) Applicant: DIC Corporation, Tokyo (JP)

(72) Inventors: Hiroshi Yoshimura, Chiba (JP); Miki Ota, Chiba (JP); Yusuke Tajiri, Chiba (JP); Osamu Suzuki, Chiba (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 15/516,181

(22) PCT Filed: Sep. 17, 2015

(86) PCT No.: PCT/JP2015/076442
§ 371 (c)(1),
(2) Date: Mar. 31, 2017

(87) PCT Pub. No.: WO2016/052226
PCT Pub. Date: Apr. 7, 2016

(65) Prior Publication Data
US 2017/0292009 A1 Oct. 12, 2017

(30) Foreign Application Priority Data
Oct. 3, 2014 (JP) ................. 2014-204793

(51) Int. Cl.
| | |
|---|---|
| *C08L 1/12* | (2006.01) |
| *C07C 69/28* | (2006.01) |
| *C07C 69/84* | (2006.01) |
| *G02F 1/13363* | (2006.01) |
| *C08K 5/12* | (2006.01) |
| *G02B 5/30* | (2006.01) |
| *C08L 1/14* | (2006.01) |

(52) U.S. Cl.
CPC ............... *C08L 1/12* (2013.01); *C07C 69/28* (2013.01); *C07C 69/84* (2013.01); *G02B 5/3083* (2013.01); *G02F 1/13363* (2013.01); *C08K 5/12* (2013.01)

(58) Field of Classification Search
CPC ... C08L 1/12; C08L 1/14; C07C 69/02; C07C 69/848; G02B 5/3083; G02F 1/133528; G02F 2201/50; C08K 5/12; B29D 1/00788; B29K 2067/00
See application file for complete search history.

(56) References Cited

FOREIGN PATENT DOCUMENTS

| | | |
|---|---|---|
| JP | 2008-069225 A | 3/2008 |
| JP | 2010-077239 A | 4/2010 |
| JP | 2010-138379 A | 6/2010 |
| JP | 2011-116912 A | 6/2011 |
| JP | 2011-140637 A | 7/2011 |
| WO | 2014/106799 A2 | 7/2014 |
| WO | 2015/001980 A1 | 1/2015 |
| WO | 2015/019929 A1 | 2/2015 |
| WO | 2015/029436 A1 | 3/2015 |

OTHER PUBLICATIONS

International Search Report PCT/JP2015/076442 dated Dec. 8, 2015 with English translation.

*Primary Examiner* — Bijan Ahvazi
(74) *Attorney, Agent, or Firm* — McDermott Will & Emery LLP

(57) ABSTRACT

The present invention has an object to provide a compound which has excellent compatibility even with a cellulose ester resin having a low acetylation degree, is capable of providing an optical film having a high Rth value and high bleed resistance, and can be suitably used as a retardation enhancer; a cellulose ester resin composition including the compound; an optical film including the resin composition; and a liquid-crystal display device including the optical film. The present invention provides an epoxy ester compound represented by the following Formula (1) (in the formula, $R^1$ to $R^4$ each independently represent an alkyl group having 1 to 3 carbon atoms; and A's each represent an aromatic group (a1) or an aliphatic group (a2) having 1 to 4 carbon atoms, and the average presence ratio [(a1)/(a2)] of the aromatic groups (a1) to the aliphatic groups (a2) is 99.9/0.1 to 80/20 in terms of a molar ratio).

10 Claims, No Drawings

EPOXY ESTER COMPOUND, CELLULOSE ESTER RESIN COMPOSITION, OPTICAL FILM, AND LIQUID-CRYSTAL DISPLAY DEVICE

CROSS-REFERENCE TO RELATED APPLICATIONS

The present Application is the U.S. National Phase of PCT/JP2015/076442 filed Sep. 17, 2015, which claims priority to Japanese Patent Application No. 2014-204793 filed Oct. 3, 2014. The subject matter of each is incorporated herein by reference in entirety.

TECHNICAL FIELD

The present invention relates to an epoxy ester compound which has excellent compatibility with various cellulose ester resins, is capable of providing a film having a high Rth value, and can be suitably used as a retardation enhancer since it is hardly bled from the film. The present invention further relates to a cellulose ester resin composition including the compound, an optical film obtained using the composition, and a liquid-crystal display device including the optical film.

BACKGROUND ART

A cellulose ester resin (CA) film has been used as a polarizer protective film constituting a polarizing plate of a liquid-crystal display device such as televisions and notebook computers from the viewpoints that it has good transparency, optical isotropy, and toughness, and good adhesiveness to polyvinyl alcohol (hereinafter abbreviated as "PVA") which is a material of a polarizer of a liquid-crystal display device.

The liquid-crystal display device has been required to have a viewing angle improving function. In particular, it has hitherto been promoted that a liquid-crystal display device in a vertically aligned (VA) mode device performs compensation of a viewing angle by overlapping a phase difference film with a polarizer protective film in order to prevent a reduction in contrast due to light leakage in a case of being viewed in an oblique direction. In addition, recently, a polarizer protective film having a phase difference function, in which the functions of two films, a polarizer protective film and a phase difference film, are integrated into one film in order to reduce the weight and the thickness of a liquid-crystal display device, is the mainstream.

The polarizer protective film having a phase difference function expresses a phase difference in the thickness direction due to its optical anisotropy to perform viewing angle compensation of a liquid-crystal display device. Generally, it is possible to determine the phase difference degree through a retardation value. Further, the phase difference degree can be evaluated through a retardation value (hereinafter abbreviated as an "Rth value") in the thickness direction of a film.

Here, the Rth value in the thickness direction is a value defined by the following equation (1).

$$R\text{th Value} = \{(nx+ny)/2 - nz\} \times d(nm) \quad (1)$$

(in the equation, nx is a refractive index in the slow phase axis direction within the film plane, ny is a refractive index in the fast axis direction within the film plane, nz is a refractive index in the thickness direction of the film, and d is the thickness (nm) of the film).

In a case of imparting a phase difference function to a polarizer protective film, a technique in which a so-called retardation enhancer is added to the polarizer protective film so as to make an adjustment to a desired phase difference is available, and it is possible to adjust the Rth value of the polarizer protective film, depending on the amount of the retardation enhancer to be added to the polarizer protective film. Accordingly, in a case of comparison of the same addition amounts, a retardation enhancer capable of increasing the Rth value to a higher value broadens a range to which the Rth values of the polarizer protective film can be adjusted, and thus, can cope with a decrease in the thickness of the polarizer protective film. Thus, there is a demand for a material which can increase the Rth value up to a maximum.

For the adjustment to a desired phase difference, a method of selecting the kind of a cellulose ester resin which forms a main agent, in addition to the use of the retardation enhancer, is also available. Specifically, a method for making an adjustment to a desired phase difference by using a modified cellulose ester resin such as cellulose acetate propionate (CAP), or a cellulose ester resin having a low degree of substitution of an acyl group, such as diacetyl cellulose (hereinafter referred to as CA having a low acetylation degree) among the cellulose ester resins is known. In particular, the CA having a low acetylation degree has an excellent Rth expression property and is more cost-effective than CAP. From these advantages, CA having a low acetylation degree has been used as a main agent of the polarizer protective film having a phase difference function.

However, the CA having a low acetylation degree has a problem in high polarity, and correspondingly, low compatibility with the retardation enhancer, and therefore, there has been a limit on the retardation enhancer to be used. Accordingly, there has been a strong demand for a retardation enhancer having good compatibility with CA having a low acetylation degree.

Furthermore, it is necessary for the polarizer protective film to have bleed resistance while not deteriorating the clarity of an image due to occurrence of cloudiness caused by the bleeding of additives from the surface of the polarizer protective film by the heat of a backlight in a liquid-crystal display device or by the use of a liquid-crystal display device under a high temperature and a high humidity.

As the retardation enhancer which has excellent bleed resistance and can impart a high Rth value, for example, an ester compound having an end sealed with p-toluic acid, which is obtained by esterification of 1,2-propylene glycol, dimethyl terephthalate, and p-toluic acid, is known (see, for example, PTL 1). However, even though the ester compound disclosed in PTL 1 was used, a film having a sufficiently high Rth value could not be obtained.

Moreover, as a retardation enhancer which has excellent bleed resistance and can impart a high Rth value as in PTL 1, an ester compound obtained by using dimethyl 2,6-naphthalenedicarboxylate, propylene glycol, and ethylene glycol is known (see, for example, PTL 2). However, the ester compound disclosed in PTL 2 has a problem in that it has insufficient compatibility with CA having a low acetylation degree, and as a result, cloudiness occurs in the obtained film.

In addition, as a retardation enhancer which has excellent bleed resistance and can impart a high Rth value as in PTLs 1 and 2, a tetramethyl biphenol-type epoxy ester compound obtained by reacting a tetramethyl biphenol-type epoxy resin with an aromatic monocarboxylic acid is known (see, for example, PTL 3). However, the epoxy ester compound disclosed in PTL 3 has a problem in that it has insufficient compatibility with CA having a low acetylation degree, and as a result, cloudiness occurs in the obtained film as the ester compound as disclosed in PTL 2.

CITATION LIST

Patent Literature

PTL 1: JP-A 2008-069225
PTL 2: JP-A 2010-138379
PTL 3: JP-A 2011-140637

SUMMARY OF INVENTION

Technical Problem

The present invention has an object to provide a compound which has excellent compatibility with CA having a low acetylation degree, is capable of providing an optical film having a high Rth value and high bleed resistance, and can be suitably used as a retardation enhancer. The present invention has other objects to provide a cellulose ester resin composition including the compound, an optical film including the resin composition, and a liquid-crystal display device using the optical film.

Solution to Problem

The present inventors have conducted extensive studies, and as a result, have found that an epoxy ester compound (epoxy ester mixture) including an epoxy ester compound having a specific structure in a specific proportion has sufficient compatibility with CA having a low acetylation degree, and as a result, a film having excellent transparency is easily obtained, a cellulose ester resin composition which forms a material of an optical film having a high Rth value and high bleed resistance is obtained by adding the epoxy ester compound to a cellulose ester resin, the film can be suitably used in optical applications, and the like, thereby completing the present invention.

That is, the present invention provides an epoxy ester compound represented by the following Formula (1).

[Chem. 1]

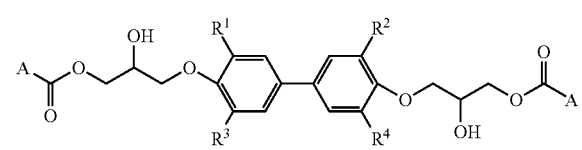

(In the formula, $R^1$ to $R^4$ each independently represent an alkyl group having 1 to 3 carbon atoms, A's each represent an aromatic group (a1) or an aliphatic group (a2) having 1 to 4 carbon atoms, and the average presence ratio [(a1)/(a2)] of the aromatic groups (a1) to the aliphatic groups (a2) is 99.9/0.1 to 80/20 in terms of a molar ratio.)

The present invention also provides a retardation enhancer which is the epoxy ester compound represented by Formula (1).

The present invention also provides a cellulose ester resin composition including the cellulose ester resin (X), the epoxy ester compound (Y), or a retardation enhancer.

The present invention also provides an optical film including the cellulose ester resin composition.

In addition, the present invention also provides a liquid-crystal display device including the optical film.

Advantageous Effects of Invention

According to the present invention, it is possible to provide an epoxy ester compound (epoxy ester mixture) which has excellent compatibility with CA having a low acetylation degree, is capable of providing an optical film having a high Rth value and high bleed resistance, and can be suitably used as a retardation enhancer. Further, according to the present invention, an optical film obtained by using the epoxy ester compound has a high Rth value, and therefore, it can be suitably used in a polarizer protective film which requires an optical compensation function. In particular, a polarizer protective film having an optical compensation function, which is used in a liquid crystal display in a vertically aligned (VA) mode, is required to have a high Rth value, and therefore, the optical film including the cellulose ester resin composition of the present invention is very useful. In addition, the epoxy ester compound of the present invention has less contamination of film forming lines caused by volatilization even at a high temperature due to its high bleed resistance, maintenance frequency can be reduced, and thus, production efficiency can also be improved.

DESCRIPTION OF EMBODIMENTS

The epoxy ester compound of the present invention is represented by the following General Formula (1).

[Chem. 2]

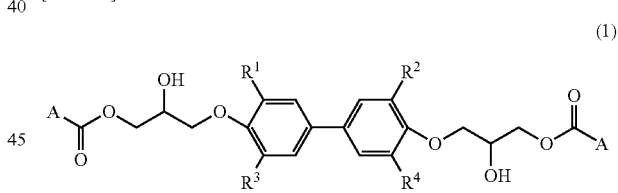

(In the formula, $R^1$ to $R^4$ each independently represent an alkyl group having 1 to 3 carbon atoms, A's each represent an aromatic group (a1) or an aliphatic group (a2) having 1 to 4 carbon atoms, and the average presence ratio [(a1)/(a2)] of the aromatic groups (a1) to the aliphatic groups (a2) is 99.9/0.1 to 80/20 in terms of a molar ratio.)

If the molar amount of the aromatic groups (a1) increases with the average presence ratio [(a1)/(a2)] of the aromatic groups (a1) to the aliphatic groups (a2) departing from the ratio of 99.9/0.1 in terms of a molar ratio, the compatibilizing effect with CA having a low acetylation degree due to a combined use of the aliphatic monocarboxylic acid is faded, and thus, cloudiness easily occurs in the obtained film, which is thus not preferable. Further, if the molar amount of the aromatic groups (a1) decreases with the average presence ratio [(a1)/(a2)] of the aromatic groups (a1) to the aliphatic groups (a2) departing from the ratio of 80/20 in terms of a molar ratio, the amount of the aromatic rings decreases, and thus, Rth expression properties are insufficient, which is thus not preferable. The average presence ratio [(a1)/(a2)] of the aromatic groups (a1) to the aliphatic groups (a2) is preferably 99/1 to 82/18, and more preferably 98/2 to 85/15, in terms of a molar ratio.

$R^1$ to $R^4$ in General Formula (1) each independently represent an alkyl group having 1 to 3 carbon atoms. Among these, a methyl group is preferable from the viewpoints that the compatibility with CA having a low acetylation degree is good, a higher retardation value (Rth value) in the thickness direction is expressed, and materials are easily available.

The aromatic group (a1) may have a substituent. Examples of the aromatic group (a1) include a phenyl group, a dimethylphenyl group, a trimethylphenyl group, a tetramethylphenyl group, an ethylphenyl group, a propylphenyl group, a para-tolyl group, a meta-tolyl group, an ortho-tolyl group, a methoxyphenyl group, an ethoxyphenyl group, a propoxyphenyl group, a cyanophenyl group, a fluorophenyl group, a nitrophenyl group, a phenylphenyl group, a methylphenylphenyl group, a dimethylphenylphenyl group, and a naphthyl group. Among these, a phenyl group, a para-tolyl group, a meta-tolyl group, or an ortho-tolyl group is preferable from the viewpoint that an epoxy ester compound having good compatibility with CA having a low acetylation degree is obtained.

Examples of the aliphatic group (a2) include a methyl group, an ethyl group, a propyl group, and a butyl group. Among these, a methyl group, an ethyl group, or a propyl group is preferable from the viewpoints that an epoxy ester compound having good compatibility with CA having a low acetylation degree is obtained and excess acid raw materials during the production are easily removed under reduced pressure.

In the epoxy ester represented by General Formula (1), $R^1$ to $R^4$ each independently represent an alkyl group having 1 to 3 carbon atoms. Among these, a methyl group is preferable from the viewpoints that the compatibility with a cellulose ester resin is good, a higher Rth value in the thickness direction is expressed, and raw materials when obtaining the epoxy ester represented by General Formula (1) is easily available.

As described above, the epoxy ester compound of the present invention has the aromatic groups (a1) and the aliphatic groups (a2) having 1 to 4 carbon atoms, and the presence ratio thereof is 99.9/0.1 to 80/20 in terms of a molar ratio. Here, the epoxy ester compound of the present invention is usually a mixture of the epoxy ester compounds having various groups as A in General Formula (1). Accordingly, the presence ratio of the aromatic groups (a1) to the aliphatic groups (a2) refers to a presence ratio (average presence ratio) in the mixture, considering the epoxy ester compound of the present invention as a mixture, not the presence ratio of the aromatic groups (a1) to the aliphatic groups (a2) in the individual compounds. Further, examples of the epoxy ester compound of the present invention include a mixture of the compounds (A1) to (A3) shown below.

An epoxy ester compound (A1) represented by Formula (1), in which one end is an aromatic group (a1) and the other end is an aliphatic group (a2).
An epoxy ester compound (A21) represented by Formula (1), in which both ends are aromatic groups (a1).
An epoxy ester compound (A3) represented by Formula (1), in which both ends are aliphatic groups (a2).
The epoxy ester compounds (A1) to (A3) may have the same or different aromatic groups (a1) or aliphatic groups (a2). Further, the epoxy ester compound of the present invention may not have all of the epoxy ester compounds (A1) to (A3), and may be, for example, a mixture of the epoxy compound (A1) and the epoxy compound (A2), a mixture of the epoxy compound (A1) and the epoxy compound (A3), or a mixture of the epoxy compound (A2) and the epoxy compound (A3).

The epoxy ester compound of the present invention can be obtained by the methods shown below, for example.

Production Method 1: The aromatic monocarboxylic acid (α1) and the aliphatic monocarboxylic acid (α2) having 1 to 4 carbon atoms are used in a proportion such that the average presence ratio of the aromatic groups (a1) to the aliphatic groups (a2) contained in the obtained epoxy ester compound consequently is 99.9/0.1 to 80/20 in terms of a molar ratio. Further, the aromatic monocarboxylic acid (α1), the aliphatic monocarboxylic acid (α2), the biphenyl skeleton, and the compound (α3) having a glycidyl ether groups at the 4 and 4' carbon atoms of the biphenyl skeleton are introduced in bulk and reacted.

Production Method 2: The aromatic monocarboxylic acid (α1) and the aliphatic monocarboxylic acid (α2) having 1 to 4 carbon atoms are used in a proportion such that the average presence ratio of the aromatic groups (a1) to the aliphatic groups (a2) contained in the obtained epoxy ester compound consequently is 99.9/0.1 to 80/20 in terms of a molar ratio. Further, the aromatic monocarboxylic acid (α1) and the compound (α3) are reacted in a reaction system in a proportion such that the glycidyl ether groups contained in the compound (α3) remain, the aliphatic monocarboxylic acid (α2) is then added to the reaction system, and the remaining glycidyl ether group and the carboxyl group of the aliphatic monocarboxylic acid (α2) are reacted.

Production Method 3: The aromatic monocarboxylic acid (α1) and the aliphatic monocarboxylic acid (α2) having 1 to 4 carbon atoms are used in a proportion such that the average presence ratio of the aromatic groups (a1) to the aliphatic groups (a2) contained in the obtained epoxy ester compound consequently is 99.9/0.1 to 80/20 in terms of a molar ratio. Further, the aliphatic monocarboxylic acid (α2) and the compound (α3) are reacted in a reaction system in a proportion such that the glycidyl ether groups contained in the compound (α3) remain, the aromatic monocarboxylic acid (α1) is then added to the reaction system, and the remaining glycidyl ether group and the carboxyl group of the aromatic monocarboxylic acid (α1) are reacted.

Production Method 4: The aromatic monocarboxylic acid (α1) and the compound (α3) are reacted to obtain an epoxy ester compound (A2) represented by Formula (1), in which both ends are aromatic groups (a1). Separately, the aliphatic monocarboxylic acid (α2) having 1 to 4 carbon atoms and the compound (α3) are reacted to obtain an epoxy ester compound (A3) represented by Formula (1), in which both ends are aliphatic groups (a2). Further, the epoxy ester compound (A2) and the epoxy ester compound (A3) are mixed in a proportion such that the average presence ratio of the aromatic groups (a1) to the aliphatic groups (a2) is 99.9/0.1 to 80/20 in terms of a molar ratio.

Here, in the present invention, the "number of carbon atoms" refers to the number of carbon atoms which do not include carbonyl carbon.

When the glycidyl ether group remains in the epoxy ester compound of the present invention, mutagenicity easily occurs, and therefore, the epoxy equivalent is preferably 50,000 g/eq. or more since mutagenicity for the epoxy compound is hard to occur, and the epoxy equivalent is more preferably 100,000 g/eq. or more.

When the carboxylic acid residue remains in the epoxy ester compound of the present invention, the hydrolysis of the cellulose ester film is promoted, which is thus not preferable. When the acid value is 1.5 mgKOH/g or less, it is difficult to promote the hydrolysis of the cellulose ester film, which is thus preferable, and the acid value may be 1.0 mgKOH/g or less.

In order to eliminate both the glycidyl ether group and the carboxylic acid group in the epoxy ester compound of the present invention, the glycidyl ether group is eliminated as the excess monocarboxylic acid starting material, and the excess monocarboxylic acid is preferably eliminated using a technique of evaporation under reduced pressure. Among the production methods, the production method 2 in which the aliphatic monocarboxylic acid (α2) having 1 to 4 carbon atoms is added later is preferable, from the viewpoint that evaporation can be easily performed during the above-mentioned evaporation of under reduced pressure.

Examples of the aromatic monocarboxylic acid (α1) include benzoic acid, dimethylbenzoic acid, trimethylbenzoic acid, tetramethylbenzoic acid, ethylbenzoic acid, propylbenzoic acid, cumic acid, o-toluic acid, m-toluic acid, p-toluic acid, anisic acid, ethoxybenzoic acid, propoxybenzoic acid, cyanobenzoic acid, fluorobenzoic acid, nitrobenzoic acid, 4-phenylbenzoic acid, 4-(3-methylphenyl)benzoic acid, 4-(4-methylphenyl)benzoic acid, 4-(3,5-dimethylphenyl)benzoic acid, 2-methyl-4-phenylbenzoic acid, 2,6-dimethyl-4-phenylbenzoic acid, 2,6-dimethyl-4-(3,5-dimethylphenyl)benzoic acid, naphthoic acid, nicotinic acid, furoic acid, 1-naphthalenecarboxylic acid, and 2-naphthalenecarboxylic acid. Among those, benzoic acid, para-toluic acid, meta-toluic acid, or ortho-toluic acid is preferable, from the viewpoint that compatibility with an epoxy ester compound having good compatibility with CA having a low acetylation degree is obtained. These aromatic monocarboxylic acid (α1) may be used singly or in combination of two or more kinds thereof.

Examples of the aliphatic monocarboxylic acid (α2) having 1 to 4 carbon atoms include acetic acid, propionic acid, butyric acid, and valeric acid. Among those, acetic acid, propionic acid, or butyric acid is preferable, from the viewpoints that an epoxy ester compound having good compatibility with CA having a low acetylation degree is obtained, and excess portions are easily removed under reduced pressure during the production. These aliphatic monocarboxylic acids (α2) may be used singly or in combination of two or more kinds thereof.

Examples of the compound (α3) having a biphenyl skeleton and glycidyl ether groups at the 4 and 4' carbon atoms of the biphenyl skeleton include diglycidyl ether-type epoxy compounds obtained by reacting biphenols having a biphenyl skeleton and hydroxyl groups at the 4 and 4' carbon atoms of the biphenyl skeleton with epichlorohydrin. Specific examples of the epoxy compound include biphenol-type epoxy compounds such as 3,3',5,5'-tetramethyl-4,4'-diglycidyl oxybiphenyl (commercially available products thereof including "jER YX-4000" (an epoxy equivalent of 180 to 192), manufactured by Mitsubishi Chemical Corporation).

In the production method 1, the reaction temperature at the time of introducing and reacting the aromatic monocarboxylic acid (α1), the aliphatic monocarboxylic acid (α2), and the compound (α3) in bulk is preferably 80° C. to 160° C., and more preferably 100° C. to 150° C. The reaction time is preferably in a range of 5 to 40 hours.

In the production method 2, the reaction temperature at the time of reacting the aromatic monocarboxylic acid (α1) with the compound (α3) is preferably 80° C. to 140° C., and more preferably 90° C. to 120° C. The reaction time is preferably in a range of 5 to 30 hours. Further, the aromatic monocarboxylic acid (α1) and the compound (α3) are reacted, and then the reaction temperature at the time of reacting the obtained reactant with the aliphatic monocarboxylic acid (α2) is preferably 100° C. to 160° C., and more preferably 120° C. to 150° C. The reaction time is preferably in a range of 1 to 10 hours.

In the production method 3, the reaction temperature at the time of reacting the aliphatic monocarboxylic acid (α2) with the compound (α3) is preferably 80° C. to 140° C., and more preferably 90° C. to 120° C. The reaction time is preferably in a range of 5 to 30 hours. Further, the reaction temperature at the time of reacting the aliphatic monocarboxylic acid (α2) and the compound (α3), and then reacting the obtained reactant and the aromatic monocarboxylic acid (α1) is preferably 100° C. to 160° C., and more preferably 120° C. to 150° C. The reaction time is preferably in a range of 1 to 10 hours.

In the production methods 1 to 3, the ratio of the compound (α3), the aromatic monocarboxylic acid (α1), and the aliphatic monocarboxylic acid (α2) to be introduced is preferably in a range such that the ratio (number of moles of the epoxy groups)/(number of moles of the carboxyl groups) of the number of moles of the epoxy groups of the compound (α3) to the number of moles of the total carboxyl groups of the aromatic monocarboxylic acid (α1) and the aliphatic monocarboxylic acid (α2) is preferably in a range of 0.8 to 1.0/1.0.

In the reaction of the epoxy group of the compound (α3), the aromatic monocarboxylic acid (α1), and the carboxyl group of the aliphatic monocarboxylic acid (α2), a catalyst may be used, if desired. Examples of the catalyst include phosphine compounds such as trimethylphosphine, triethylphosphine, tributylphosphine, trioctylphosphine, and triphenylphosphine; imidazole-based compounds such as 2-methylimidazole, 2-ethylimidazole, 2-isopropylimidazole, 2-ethyl-4-methylimidazole, and 4-phenyl-2-methylimidazole; amine compounds such as triethylamine, tributylamine, trihexylamine, triamylamine, triethanolamine, dimethylaminoethanol, triethylendiamine, dimethylphenylamine, dimethylbenzylamine, 2-(dimethylaminomethyl)phenol, and 1,8-diazabicyclo(5,4,0)undecene-7; and pyridine compounds such as dimethylaminopyridine. These catalysts are preferably used in a proportion of 0.05 to 1 part by mass, with respect to 100 parts by mass of the compound (α3), the aromatic monocarboxylic acid (α1), and the aliphatic monocarboxylic acid (α2).

As described above, the epoxy ester compound represented by Formula (1) can be preferably used, particularly as a retardation enhancer. Further, the cellulose ester resin composition of the present invention may contain the cellulose ester resin (X), the epoxy ester compound (mixture) (Y) of the present invention, or a retardation enhancer.

The cellulose ester resin (X) is a product of esterification of a part or all of hydroxyl groups contained in the cellulose obtained from cotton linter, wood pulp, kenaf, or the like. Among these, films obtained using the obtained cellulose ester resin is easily peeled from a metal support constituting a device for producing the film, and thus, it is possible to improve the production efficiency of the film, which is thus preferable.

Specific examples of the cellulose ester resin (X) include cellulose acetate, cellulose acetate propionate, cellulose acetate butyrate, cellulose acetate propionate butyrate, cellulose acetate phthalate, and cellulose nitrate. These cellulose ester resins may be used singly or in combination of two or more kinds thereof. In a case of using a film formed of the cellulose ester resin composition of the present invention as an optical film, particularly a polarizer protective film having a phase difference function, it is preferable to use cellulose acetate having a low acetylation degree since it is easy to make an adjustment to a high phase difference value, and it is possible to obtain a film having excellent mechanic properties and transparency.

As the cellulose acetate, those having an average acetylation degree (amount of the acetic acid bonded) in a range of 50.0% to 62.5% by mass are preferable since that an optical film including the obtained cellulose ester resin composition forms a film having excellent mechanic properties and transparency.

Furthermore, in order to improve the resistance to moisture permeation of an optical film, it is preferable that the average acetylation degree of cellulose acetate is in a range of 54% to 61.5% by mass. Further, in order to make an adjustment to a high phase difference value, it is preferable that the optical film has an average acetylation degree of cellulose acetate in a range of 50.0% to 58% by mass.

Furthermore, the average acetylation degree is a mass ratio of acetic acid produced by saponification of cellulose acetate, based on the mass of the cellulose acetate.

The cellulose ester resin (X) preferably has a number-average molecular weight in a range of 30,000 to 300,000 since it can improve the mechanic properties of the film. Further, in a case where higher mechanic properties are required, the cellulose ester resin (X) having a number-average molecular weight in a range of 50,000 to 200,000 is more preferably used.

Here, in the present invention, the weight-average molecular weight (Mw) and the number-average molecular weight (Mn) are values determined in terms of polystyrene on the basis of GPC measurement. Further, the measurement conditions for GPC are as follows.

[Conditions for GPC Measurement]
Measurement apparatus: High-speed GPC apparatus "HLC-8320GPC" manufactured by Tosoh Corporation
Column: "TSK GURDCOLUMN SuperHZ-L" manufactured by Tosoh Corporation
+"TSK gel SuperHZM-M" manufactured by Tosoh Corporation
+"TSK gel SuperHZM-M" manufactured by Tosoh Corporation
+"TSK gel SuperHZ-2000" manufactured by Tosoh Corporation
+"TSK gel SuperHZ-2000" manufactured by Tosoh Corporation
Detector: Differential refractometer (RI)
Data processing: "EcoSEC Data Analysis version 1.07" manufactured by Tosoh Corporation
Column temperature: 40° C.
Eluent: Tetrahydrofuran
Flow rate: 0.35 mL/min
Measurement sample: A measurement sample is prepared by dissolving 15 mg of a sample in 10 ml of tetrahydrofuran and filtering the obtained solution through a microfilter.
Amount of sample injected: 20 µl
Reference samples: The following monodisperse polystyrenes having known molecular weights were used in accordance with the measurement manual of "HLC-8320GPC".
(Monodisperse Polystyrene)
"A-300" manufactured by Tosoh Corporation
"A-500" manufactured by Tosoh Corporation
"A-1000" manufactured by Tosoh Corporation
"A-2500" manufactured by Tosoh Corporation
"A-5000" manufactured by Tosoh Corporation
"F-1" manufactured by Tosoh Corporation
"F-2" manufactured by Tosoh Corporation
"F-4" manufactured by Tosoh Corporation
"F-10" manufactured by Tosoh Corporation
"F-20" manufactured by Tosoh Corporation
"F-40" manufactured by Tosoh Corporation
"F-80" manufactured by Tosoh Corporation
"F-128" manufactured by Tosoh Corporation
"F-288" manufactured by Tosoh Corporation When the cellulose ester resin composition of the present invention includes the epoxy ester compound (Y) or the retardation enhancer in the proportion in a range of 0.5 to 30 parts by mass with respect to 100 parts by mass of the cellulose ester resin (X), a high phase difference function and a low moisture permeability can be imparted, and the volatility with which the components are volatilized from the resin composition can be reduced even under high temperature and high humidity, which is thus preferable. Further, in a case of reducing the volatility and imparting a high phase difference function and a low moisture permeability, the epoxy ester compound (Y) or the retardation enhancer is more preferably contained in the proportion in a range of 1 to 20 parts by mass, with respect to 100 parts by mass of the cellulose ester resin (X).

Furthermore, in the cellulose ester resin composition of the present invention, various additives of the epoxy ester compound (Y) or the retardation enhancer can be added to the cellulose ester resin (X), within a range not interfering with the effect of the present invention.

Examples of the various additives include a modifier (also including a plasticizer), an ultraviolet rays absorber, a retardation enhancer other than the retardation enhancer of the present invention, a resin, a matting agent, an anti-degradation agent (for example, an antioxidant, a peroxide decomposer, a radical inhibitor, a metal inactivating agent, and an acid scavenger), and a dye. Further, these additives can also be added when dissolving and mixing the cellulose ester resin (X), the epoxy ester compound (Y), or the retardation enhancer in an organic solvent in the absorber casting method which will be described later.

Examples of the modifier (also including a plasticizer) include phosphoric esters such as triphenyl phosphate, tricresyl phosphate, and cresyl diphenyl phosphate; phthalic esters such as dimethyl phthalate, diethyl phthalate, dibutyl phthalate, and di-2-ethylhexyl phthalate; ethyl phthalyl ethyl glycolate, butyl phthalyl butyl glycolate, trimethylolpropane tribenzoate, pentaerythritol tetraacetate, and tributyl acetyl-citrate.

Examples of the ultraviolet ray absorber include oxybenzophenone-based compounds, benzotriazole-based compounds, salicylic ester-based compounds, benzophenone compounds, cyanoacrylate-based compounds, and nickel complex salt-based compounds. The amount of the ultraviolet ray absorber to be added is preferably in a range of 0.01 to 2 parts by mass with respect to 100 parts by mass of the cellulose ester resin (X).

The retardation enhancer other than the retardation enhancer of the present invention is not limited in any way as long as it increases the retardation value (Rth value), but examples thereof include liquid crystal compounds such as 4-cyano-4-pentylbiphenyl, 1,4-cyclohexanedicarboxylic acid ester compounds, and compounds having 1,3,5-triazine rings. The amount of the retardation enhancer to be added is preferably in a range of 0.01 to 20 parts by mass, and in particular, more preferably 1 to 10 parts by mass, with respect to 100 parts by mass of the cellulose ester resin (X).

Examples of the resin which is used as the additive include polyester resins (for example, polyethylene terephthalate and methyl polymethacrylate), polycarbonate resins, polyester ether resins, polyurethane resins, epoxy resins, and toluenesulfonamide resins.

Examples of the matting agent include silicon oxide, titanium oxide, aluminum oxide, calcium carbonate, calcium silicate, aluminum silicate, magnesium silicate, calcium phosphate, kaoline, and talc. The amount of the matting agent is preferably in a range of 0.1 to 0.3 parts by mass with respect to 100 parts by mass of the cellulose ester resin (A).

As the dye, known dyes that are usually used can be used, and is not particularly limited in terms of the amount of addition within a range not interfering with the object of the present invention.

The cellulose ester resin composition of the present invention can be used in an optical film. The optical film of the present invention can be obtained by molding the cellulose ester resin composition into a film. Examples of the molding method include a method in which the cellulose ester resin composition of the present invention is melt-kneaded with an extruder or the like, and molded into a film by using a T-die or the like.

Furthermore, the optical film of the present invention can also be obtained by, in addition to the molding method, an absorber casting method in which the cellulose ester resin composition is uniformly dissolved and mixed in an organic solvent, and the obtained resin solution is cast and dried on a metal support. In a case of obtaining a film by the absorber casting method, it is possible to suppress the orientation of the cellulose ester resin (A) in the film in the middle of the molding. Therefore, the obtained film substantially exhibits optical isotropy. The film exhibiting the optical isotropy can be used as a member such as a liquid crystal display and as an optical film, and is particularly useful as a polarizer protective film. Further, the film obtained by the absorber casting method is hardly uneven on the surface, and the absorber casting method is a more preferred method for forming a film since it has characteristics of excellent surface smoothness.

The absorber casting method includes a first step of dissolving the cellulose ester resin (X) and the epoxy ester compound (Y) in an organic solvent, and casting the obtained resin solution on a metal support, a second step of drying the organic solvent included in the cast resin solution to form a film, and a third step of peeling the film formed on the metal support from the metal support, and heating and drying the film.

As the metal support used in the first step, a metal support formed of a metal having the shape of an endless belt or a drum, for example, a metal support formed of stainless steel and having a mirror-finish surface can be used. For the casting of the resin solution onto the metal support, a resin solution having been filtered through a filter is preferably used in order to prevent foreign matter from being incorporated into the obtained film.

As the drying method in the second step, there is, for example, a method in which air at a temperature in a range from 30° C. to 50° C. is blown onto the upper and lower surfaces of the metal support such that approximately 50% to 80% by mass of the organic solvent included in the cast resin solution is evaporated, thereby forming a film on the metal support.

The third step is a step of peeling the film formed in the second step from the metal support, and heating and drying the film at a higher temperature than that in the step 2. As the heating and drying method, a method in which the temperature is raised at a temperature in a range from 100° C. to 160° C. in stages is preferable since good dimensional stability is improved. By heating and drying the film at a temperature in the range, the organic solvent which remains in the film obtained in the second step can be substantially completely removed.

The concentration of the non-volatilized fractions in the resin solution is preferably in a range of 3% to 50% by mass, and more preferably in a range of 5% to 40% by mass.

The organic solvent is not particularly limited as long as it can dissolve the cellulose ester resin (X) and the epoxy ester compound (Y), but for example, in a case where cellulose acetate is used as the cellulose ester resin (X), for example, an organic halogen compound such as methylene chloride, or a dioxolane can be used as a good solvent for cellulose acetate. Further, it is preferable to use a poor solvent such as methanol, ethanol, 2-propanol, n-butanol, cyclohexane, and cyclohexanone in combination with the good solvent in order to improve the production efficiency for the film. In a case of using the good solvent to the poor solvent after mixing them, the mixing ratio of the two solvents, the good solvent/the poor solvent, is preferably in a range of 75/25 to 95/5 (% by mass).

The film thickness of the optical film of the present invention is preferably in a range of 10 to 100 μm. In a case of using film as a polarizer protective film among the optical films, when the film thickness is in a range of 15 to 80 μm, it is possible to obtain a liquid-crystal display device having a small thickness, and excellent film strength, dimensional stability due to a change in humidity and heat, and resistance to moisture permeation can be maintained.

Moreover, the optical film of the present invention can be used in a polarizer protective film having an optical compensation function. The polarizer protective film is required to have anisotropy in a specific range, depending on a liquid crystal display mode such as a twisted nematic (TN) mode, a vertically aligned (VA) mode, and an optically compensatory bend (OCB) mode. In particular, the optical film of the present invention can be suitably used in a polarizer protective film to which an optical compensation function has been imparted, used in a liquid crystal display in a VA mode.

The optical film of the present invention preferably has an Rth value of 100 nm or more, and more preferably has an Rth value in a range of 100 to 500 nm since it can compensate the phase difference derived from the liquid crystal material effectively.

In order to obtain a polarizer protective film having desired optical anisotropy, the amount of the epoxy ester compound (Y) or the retardation enhancer to be added to the cellulose ester resin composition of the present invention can be adjusted to obtain the film. In particular, since the epoxy ester compound (Y) used in the present invention makes it possible to achieve a high Rth value with a small addition amount thereof, an adjustment to a desired Rth value can be made after reducing the volatility even in a liquid-crystal display device for which a liquid crystal display mode such as VA, OCB, and TN, requiring a relatively high Rth value, is adopted.

In a case where the film thickness of the optical film is 60 μm, the moisture permeability of a film composed only of the cellulose ester resin (X) varies depending on the kind of the cellulose ester resin, but is approximately 950 to 1300 g/m²·24 h. A moisture permeability of 900 g/m²·24 h or less is preferable since the optical film including the cellulose ester resin composition of the present invention, to which the epoxy ester compound (Y) has added, can suppress the adverse effects of moisture upon forming into a polarizing plate, and a moisture permeability is 100 to 800 g/m²·24 h is more preferable.

The optical film of the present invention can be used in, for example, an optical film of a liquid-crystal display device or a support of a photosensitive material for silver halide photography since it has high resistance to moisture permeation, high transparency, low volatility, and the like as well as high optical performance. Here, examples of the optical film include a polarizer protective film, a phase difference film, a reflecting plate, a diffusion film, a viewing angle improving film, an antiglare film, an antireflection film, an antistatic film, and a color filter. Among these optical films, in addition to excellent characteristics as described above, an optical film having a high Rth value can be used as a polarizer protective film having a viewing angle compensation function.

Examples of the liquid-crystal display device of the present invention include those having a polarizing plate for a liquid-crystal display device including the optical film of the present invention. Specifically, the polarizing plate for a liquid-crystal display device has a structure in which the optical film of the present invention as a polarizer protective film is attached to one side or both sides of a polarizer in which dichroic molecules of iodine compounds or the like are oriented in a polyvinyl alcohol (PVA) film. Further, this polarizing plate for a liquid-crystal display device is arranged in a state of crossed nicols on both sides of a liquid crystal cell.

EXAMPLES

Hereinafter, the present invention will be more specifically described on the basis of Examples. In Examples, parts and % are on a mass basis unless otherwise specified.

Example 1

Into a 3-liter 4-neck flask equipped with a thermometer, a stirrer, and a reflux condenser, 1,337 g of tetramethyl biphenol-type epoxy resin (an epoxy equivalent of 191 g/eq.), 905 g of para-toluic acid, 449 g of methyl isobutyl ketone as a solvent, and 2 g of triphenylphosphine as a catalyst were charged, and the mixture was reacted at 115° C. for 9 hours. Subsequently, 56 g of acetic acid was added thereto, and the mixture was warmed to 140° C. and reacted at 140° C. for 4 hours. Unreacted raw materials were removed at 140° C. and 0.005 MPa to obtain the epoxy ester compound (epoxy ester mixture) (1) of the present invention, represented by Formula (1).

For the epoxy ester compound (1), the acid value was 0.43 mgKOH/g, the epoxy equivalent was 350,000 g/eq., the hydroxyl value was 172 mgKOH/g, and the number-average molecular weight was 690. The average presence ratio (para-tolyl groups/methyl groups) of the aromatic groups (a1) (para-tolyl groups) to the aliphatic groups (a2) (methyl groups) contained in the epoxy ester compound (1) in terms of a molar ratio was 96/4. Here, the acid value, the epoxy equivalents, the hydroxyl value, and the average presence ratio of the para-tolyl group to the methyl group were determined by the following methods (the same shall apply hereinafter).

Acid value: Measured in accordance with JIS K 0070-1992.

Epoxy equivalents: Measured in accordance with JIS K 7236: 2001.

Hydroxyl value: Measured in accordance with JIS K 0070-1992.

Average presence ratio of the aromatic groups (a1) to the aliphatic groups (a2): Measured by means of $^{13}$CNMR.

<Measurement Conditions for $^{13}$CNMR>

Instrument name: "JNM-ECA500" manufactured by Nippon Electronics Co., Ltd.

Sample concentration: 30% (w/v)

Measurement solvent: Deuterated chloroform (CDCl$_3$)

Cumulative number of times: 4,000 times

Next, 810 parts of methylene chloride and 90 parts of methanol were added to 100 parts of diacetyl cellulose (trade name L-50, an acetylation degree of 55%, manufactured by Daicel Chemical Industries, Ltd.), and 10 parts of the epoxy ester compound (1), and dissolved therein to obtain a dope solution. The dope solution was cast on a glass plate such that it had a thickness of about 0.8 mm, left to stand overnight at room temperature, and dried at 50° C. for 30 minutes and at 120° C. for 30 minutes to obtain a film having a film thickness of 60 μm.

Using the obtained film, the compatibility with a cellulose ester resin, the bleed resistance, the retardation value (Rth value) in the thickness direction, and the resistance to moisture permeation of the epoxy ester compound (1) of the present invention were evaluated by the following methods. The results are shown in Table 1.

<Method for Evaluating Compatibility>

The haze value of the film was measured in accordance with JIS K 7105, using a haze meter ("NDH 5000" manufactured by Nippon Denshoku Industries Co., Ltd.). The smaller the value, the higher the transparency and the higher the compatibility.

<Method for Evaluating Bleed Resistance>

The film was left to stand at a constant temperature and a constant humidity of a temperature 85° C. and a relative humidity of 90% for 5 days, and then the haze value of the film was measured according to <Method for Evaluating Compatibility>. The smaller the value, the higher the transparency and the more excellent the bleed resistance.

<Method of Evaluating Rth>

The retardation value (Rth value) of the film in the thickness direction was measured by a parallel Nicol rotation method, using a phase difference measurement apparatus KOBRA-WR (manufactured by Oji Scientific Instruments). Further, the film which had been left to stand at 23° C. and 55% RH for 1 hour or longer was used for the measurement.

<Method of Evaluating Resistance to Moisture Permeation>

The resistance to moisture permeation was measured according to the method described in JIS Z 0208. The measurement conditions were as follows: a temperature of 40° C. and a relative humidity of 90%. The smaller the obtained value, the more excellent resistance to moisture permeation.

In addition, triacetyl cellulose (trade name LT-35, an acetylation degree of 61%, manufactured by Daicel Chemical Industries, Ltd.) was used instead of diacetyl cellulose to measure the film, and the compatibility with a cellulose ester resin, the bleed resistance, the retardation value (Rth value) in the thickness direction, and the resistance to moisture permeation were evaluated according to the following methods. The results are shown in Table 1.

Example 2

Into a 3-liter 4-neck flask equipped with a thermometer, a stirrer, and a reflux condenser, 1,337 g of tetramethyl biphenol-type epoxy resin (an epoxy equivalent of 191 g/eq.), 905 g of para-toluic acid, 448 g of methyl isobutyl ketone as a solvent, and 2 g of triphenylphosphine as a catalyst were charged, and the mixture was reacted at 115° C. for 10 hours. Subsequently, 112 g of propionic acid was added thereto, and the mixture was warmed to 140° C. and reacted at 140° C. for 5 hours. Unreacted raw materials were removed at 140° C. and 0.005 MPa to obtain the epoxy ester compound (epoxy ester mixture) (2) of the present invention, represented by Formula (1).

For the epoxy ester compound (2), the acid value was 0.52 mgKOH/g, the epoxy equivalent was 180,000 g/eq., the hydroxyl value was 179 mgKOH/g, and the number-average molecular weight was 690. The average presence ratio (para-tolyl groups/ethyl groups) of the aromatic groups (a1) (para-tolyl groups) to the aliphatic groups (a2) (ethyl groups) contained in the epoxy ester compound (2) in terms of a molar ratio was 96/4.

In the same manner as in Example 1, a film was manufactured, and the compatibility of the epoxy ester compound (2) with a cellulose ester resin, the bleed resistance, the retardation value (Rth value) in the thickness direction, and the resistance to moisture permeation were evaluated according to the following methods. The results are shown in Table 1.

Example 3

Into a 3-liter 4-neck flask equipped with a thermometer, a stirrer, and a reflux condenser, 430 g of tetramethyl biphenol-type epoxy resin (an epoxy equivalent of 191 g/eq.), 261 g of benzoic acid, 138 g of methyl isobutyl ketone as a solvent, and 0.7 g of triphenylphosphine as a catalyst were charged, and the mixture was reacted at 115° C. for 24 hours. Subsequently, 17 g of acetic acid was added thereto, and the mixture was warmed to 140° C. and reacted at 140° C. for 6 hours. Unreacted raw materials were removed at 140° C. and 0.005 MPa to obtain the epoxy ester compound (epoxy ester mixture) (3) of the present invention, represented by Formula (1).

For the epoxy ester compound (3), the acid value was 0.47 mgKOH/g, the epoxy equivalent was 268,000 g/eq., the hydroxyl value was 183 mgKOH/g, and the number-average molecular weight was 690. The average presence ratio (phenyl groups/methyl groups) of the aromatic groups (a1) (phenyl groups) to the aliphatic groups (a2) (methyl groups) contained in the epoxy ester compound (3) in terms of a molar ratio was 91/9.

In the same manner as in Example 1, a film was manufactured, and the compatibility of the epoxy ester compound (3) with a cellulose ester resin, the bleed resistance, the retardation value (Rth value) in the thickness direction, and the resistance to moisture permeation were evaluated according to the following methods. The results are shown in Table 1.

Example 4

Into a 3-liter 4-neck flask equipped with a thermometer, a stirrer, and a reflux condenser, 1,337 g of tetramethyl biphenol-type epoxy resin (an epoxy equivalent of 191 g/eq.), 905 g of meta-toluic acid, 449 g of methyl isobutyl ketone as a solvent, and 2 g of triphenylphosphine as a catalyst were charged, and the mixture was reacted at 115° C. for 17 hours. Subsequently, 56 g of acetic acid was added thereto, and the mixture was warmed to 140° C. and reacted at 140° C. for 5 hours. Unreacted raw materials were removed at 140° C. and 0.005 MPa to obtain the epoxy ester compound (epoxy ester mixture) (4) of the present invention, represented by Formula (1).

For the epoxy ester compound (4), the acid value was 0.31 mgKOH/g, the epoxy equivalent was 140,000 g/eq., the hydroxyl value was 169 mgKOH/g, and the number-average molecular weight was 695. The average presence ratio (meta-tolyl groups/methyl groups) of the aromatic groups (a1) (meta-tolyl groups) to the aliphatic groups (a2) (methyl groups) contained in the epoxy ester compound (4) in terms of a molar ratio was 92/8.

In the same manner as in Example 1, a film was manufactured, and the compatibility of the epoxy ester compound (4) with a cellulose ester resin, the bleed resistance, the retardation value (Rth value) in the thickness direction, and the resistance to moisture permeation were evaluated according to the following methods. The results are shown in Table 2.

Example 5

Into a 3-liter 4-neck flask equipped with a thermometer, a stirrer, and a reflux condenser, 1,337 g of tetramethyl biphenol-type epoxy resin (an epoxy equivalent of 191 g/eq.), 905 g of ortho-toluic acid, 449 g of methyl isobutyl ketone as a solvent, and 2 g of triphenylphosphine as a catalyst were charged, and the mixture was reacted at 115° C. for 13 hours. Subsequently, 112 g of butyric acid was added thereto, and the mixture was warmed to 140° C. and reacted at 140° C. for 6 hours. Unreacted raw materials were removed at 140° C. and 0.005 MPa to obtain the epoxy ester compound (epoxy ester mixture) (5) of the present invention, represented by Formula (1).

For the epoxy ester compound (5), the acid value was 0.61 mgKOH/g, the epoxy equivalent was 280,000 g/eq., the hydroxyl value was 170 mgKOH/g, and the number-average molecular weight was 710. The average presence ratio (ortho-tolyl groups/propyl groups) of the aromatic groups (a1) (ortho-tolyl groups) to the aliphatic groups (a2) (propyl groups) contained in the epoxy ester compound (5) in terms of a molar ratio was 86/14.

In the same manner as in Example 1, a film was manufactured, and the compatibility of the epoxy ester compound (4) with a cellulose ester resin, the bleed resistance, the retardation value (Rth value) in the thickness direction, and the resistance to moisture permeation were evaluated according to the following methods. The results are shown in Table 2.

Comparative Example 1

Into a 3-liter 4-neck flask equipped with a thermometer, a stirrer, and a reflux condenser, 299 g of tetramethyl biphenol-type epoxy resin (an epoxy equivalent of 187 g/eq.), 217 g of para-toluic acid, and 1 g of triphenylphosphine as a catalyst were charged, and the mixture was reacted at 115° C. for 24 hours under reduced pressure of 0.005 MPa to obtain a comparative epoxy ester compound (1').

For the comparative epoxy ester compound (1'), the acid value was 0.2 mgKOH/g, the epoxy equivalent was 28,000 g/eq., the hydroxyl value was 171 mgKOH/g, and the number-average molecular weight was 670.

In the same manner as in Example 1, a film was manufactured, and the compatibility of the comparative epoxy ester compound (1') with a cellulose ester resin, the bleed resistance, the retardation value (Rth value) in the thickness direction, and the resistance to moisture permeation were evaluated according to the following methods. The results are shown in Table 3.

Comparative Example 2

Into a 4-neck flask having an inner volume of 3 liters, equipped with a thermometer, a stirrer, and a reflux condenser, 553.5 g of dimethyl terephthalate, 476.4 g of propylene glycol, 816.6 g of para-toluic acid, and 0.111 g of tetraisopropyl titanate as an esterification catalyst were charged, and the mixture was warmed to 230° C. in stages while stirring it in a nitrogen air stream, to perform a condensation reaction for 17 hours in total. After the reaction, unreacted propylene glycol was removed under reduced pressure at 195° C. to obtain a comparative ester compound (2').

For the comparative ester compound (2'), the acid value was 0.19 mgKOH/g, the hydroxyl value was 11 mgKOH/g, and the number-average molecular weight was 450.

In the same manner as in Example 1, a film was manufactured, and the compatibility of the comparative ester compound (2') with a cellulose ester resin, the bleed resistance, the retardation value (Rth value) in the thickness direction, and the resistance to moisture permeation were evaluated according to the following methods. The results are shown in Table 3.

Comparative Example 3

Into a 4-neck flask having an inner volume of 3 liters, equipped with a thermometer, a stirrer, and a reflux condenser, 1,221 g of dimethyl 2,6-naphthalenedicarboxylate, 93 g of diethylene glycol, 1,027 g of propylene glycol, and 0.12 g of tetraisopropyl titanate as an esterification catalyst were charged, and the mixture was warmed to 205° C. in stages while stirring it in a nitrogen air stream, and reacted for 18 hours in total. After the reaction, unreacted propylene glycol was removed under reduced pressure at 160° C. to obtain a comparative ester compound (3').

For the comparative ester compound (3'), the acid value was 0.20 mgKOH/g, the hydroxyl value was 161 gKOH/g, and the number-average molecular weight was 710.

In the same manner as in Example 1, a film was manufactured, and the compatibility of the comparative epoxy ester compound (2') with a cellulose ester resin, the bleed resistance, the retardation value (Rth value) in the thickness direction, and the resistance to moisture permeation were evaluated according to the following methods. The results are shown in Table 3.

Comparative Example 4

In the same manner as in Example 1 except that the epoxy ester compound was not added, a film was manufactured, and the transparency (corresponding to evaluation of compatibility in Examples), the transparency after humidification and heating (corresponding to evaluation of bleeding properties in Examples), the retardation value (Rth value) in the thickness direction, and the resistance to moisture permeation of the film were evaluated according to the following methods. The results are shown in Table 3.

TABLE 1

|  |  | Example 1 | | Example 2 | | Example 3 | |
| --- | --- | --- | --- | --- | --- | --- | --- |
| Diacetyl cellulose (parts) |  | 100 |  | 100 |  | 100 |  |
| Triacetyl cellulose (parts) |  |  | 100 |  | 100 |  | 100 |
| Epoxy ester compound (1) (parts) |  | 10 | 10 |  |  |  |  |
| Epoxy ester compound (2) (parts) |  |  |  | 10 | 10 |  |  |
| Epoxy ester compound (3) (parts) |  |  |  |  |  | 10 | 10 |
| Epoxy ester compound (4) (parts) |  |  |  |  |  |  |  |
| Epoxy ester compound (5) (parts) |  |  |  |  |  |  |  |
| Compatibility (HAZE value) | % | 0.4 | 0.4 | 0.6 | 0.5 | 0.5 | 0.4 |
| Bleed resistance (HAZE value) | % | 0.6 | 0.5 | 0.7 | 0.4 | 0.6 | 0.5 |
| Rth value | nm | 173 | 143 | 170 | 141 | 168 | 140 |
| Resistance to moisture permeation | g/m² · 24 h | 703 | 604 | 708 | 610 | 695 | 595 |

TABLE 2

|  |  | Example 4 | | Example 5 | |
| --- | --- | --- | --- | --- | --- |
| Diacetyl cellulose (parts) |  | 100 |  | 100 |  |
| Triacetyl cellulose (parts) |  |  | 100 |  | 100 |
| Epoxy ester compound (1) (parts) |  |  |  |  |  |
| Epoxy ester compound (2) (parts) |  |  |  |  |  |
| Epoxy ester compound (3) (parts) |  |  |  |  |  |
| Epoxy ester compound (4) (parts) |  | 10 | 10 |  |  |
| Epoxy ester compound (5) (parts) |  |  |  | 10 | 10 |
| Compatibility (HAZE value) | % | 0.4 | 0.3 | 0.7 | 0.5 |
| Bleed resistance (HAZE value) | % | 0.5 | 0.5 | 0.8 | 0.7 |
| Rth value | nm | 165 | 135 | 163 | 134 |
| Resistance to moisture permeation | g/m² · 24 h | 700 | 600 | 710 | 613 |

TABLE 3

| | | Comparative Example 1 | | Comparative Example 2 | | Comparative Example 3 | | Comparative Example 4 | |
|---|---|---|---|---|---|---|---|---|---|
| Diacetyl cellulose (parts) | | 100 | | 100 | | 100 | | 100 | |
| Triacetyl cellulose (parts) | | | 100 | | 100 | | 100 | | 100 |
| Epoxy ester compound (1') (parts) | | 10 | 10 | | | | | | |
| Epoxy ester compound (2') (parts) | | | | 10 | 10 | | | | |
| Epoxy ester compound (3') (parts) | | | | | | 10 | 10 | | |
| Compatibility (HAZE value) | % | 2 | 0.4 | 0.4 | 0.4 | 24 | 0.4 | 0.4 | 0.4 |
| Bleed resistance (HAZE value) | % | 4.5 | 0.8 | 0.5 | 0.5 | 30 | 0.4 | 0.5 | 0.4 |
| Rth value | nm | 162 | 137 | 127 | 70 | 186 | 128 | 115 | 20 |
| Resistance to moisture permeation | g/m² · 24 h | 720 | 621 | 692 | 540 | 760 | 660 | 1251 | 990 |

It can be seen that for the film obtained using the epoxy ester compound of the present invention, shown in Examples 1 to 5, the HAZE value in a case of adding the epoxy ester compound to diacetyl cellulose (CA having a low acetylation degree) and the HAZE value after the wet heat test are 1% or less, and the epoxy ester compound of the present invention has excellent compatibility or bleed resistance. In addition, it can also be seen that the Rth value of a film obtained in a case of adding the epoxy ester compound of the present invention to diacetyl cellulose (CA having a low acetylation degree) is as high as 163 to 173 nm, and thus, the epoxy ester compound of the present invention is highly effective as a retardation enhancer.

Comparative Example 1 is directed to a film obtained using a tetramethyl biphenol-type epoxy ester compound obtained by the reaction of a tetramethyl biphenol-type epoxy resin with an aromatic monocarboxylic acid, which falls in the related art. It can be seen that the HAZE value of a film obtained by adding the tetramethyl biphenol-type epoxy ester compound to diacetyl cellulose (CA having a low acetylation degree) is 2, and thus, the tetramethyl biphenol-type epoxy ester compound has poor compatibility.

Comparative Example 2 is directed to a film obtained using an ester compound having an end sealed with p-toluic acid, obtained by esterifying 1,2-propylene glycol, dimethyl terephthalate, and p-toluic acid, which falls within the related art. It can be seen that the Rth value of a film obtained by adding the ester compound to diacetyl cellulose (CA having a low acetylation degree) is as low as 127, and thus, the ester compound is insufficient as a retardation enhancer.

Comparative Example 3 is directed to a film obtained using the ester compound which has been obtained using dimethyl 2,6-naphthalenedicarboxylate, propylene glycol, and ethylene glycol, which falls within the related art. It can be seen that the HAZE value of a film obtained by adding the ester compound to diacetyl cellulose (CA having a low acetylation degree) is as high as 24, and thus, the ester compound is poor compatibility.

The invention claimed is:

1. A mixture of epoxy ester compounds represented by the following Formula (1):

[Chem. 1]

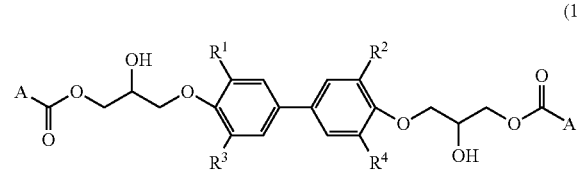

(1)

wherein $R^1$ to $R^4$ each independently represent an alkyl group having 1 to 3 carbon atoms, A's each represent an aromatic group (a1) or an aliphatic group (a2) having 1 to 4 carbon atoms, and the average presence ratio (a1):(a2) of the aromatic groups (a1) to the aliphatic groups (a2) is from 99.9:0.1 to 80:20 in terms of a molar ratio.

2. The mixture of the epoxy ester compounds according to claim 1, wherein the aromatic group (a1) is a phenyl group, a para-tolyl group, a meta-tolyl group, or an ortho-tolyl group.

3. The mixture of the epoxy ester compounds according to claim 1, wherein the aliphatic group (a2) is a methyl group, an ethyl group, or a propyl group.

4. The mixture of the epoxy ester compounds according to claim 1, wherein the average presence ratio (a1):(a2) of the aromatic groups (a1) to the aliphatic groups (a2) is from 98:2 to 85:15 in terms of a molar ratio.

5. The mixture of the epoxy ester compounds according to claim 1, wherein $R^1$ to $R^4$ are each a methyl group.

6. A cellulose ester resin composition comprising a cellulose ester resin (X) and the mixture of epoxy ester compounds (Y) according to claim 1.

7. The cellulose ester resin composition according to claim 6, wherein the mixture of epoxy ester compounds (Y) is included in the proportion of 0.5 to 30 parts by mass with respect to 100 parts by mass of the cellulose ester resin (X).

8. An optical film comprising the cellulose ester resin composition according to claim 6.

9. A liquid-crystal display device comprising the optical film according to claim 8.

10. A retardation enhancer which is a mixture of epoxy ester compounds represented by the following Formula (1):

[Chem. 2]

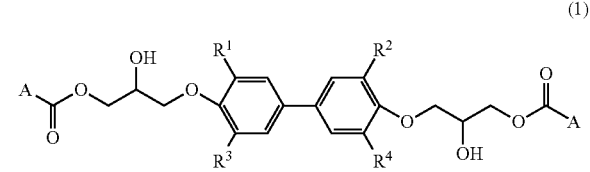

(1)

wherein $R^1$ to $R^4$ each independently represent an alkyl group having 1 to 3 carbon atoms, A's each represent an aromatic group (a1) or an aliphatic group (a2) having 1 to 4 carbon atoms, and the average presence ratio (a1):(a2) of the aromatic groups (a1) to the aliphatic groups (a2) is from 99.9:0.1 to 80:20 in terms of a molar ratio.

* * * * *